(12) United States Patent
Hornung et al.

(10) Patent No.: US 10,059,938 B2
(45) Date of Patent: Aug. 28, 2018

(54) GENE EXPRESSION ANALYSIS

(71) Applicant: Rheinische Friedrich-Wilhelms-Universität Bonn, Bonn (DE)

(72) Inventors: Veit Hornung, Bonn (DE); Jonathan Schmid-Burgk, Bonn (DE)

(73) Assignee: RHEINISCHE FRIEDRICH-WILHELMS-UNIVERSITAT BONN, Bonn (DE)

(*) Notice: Subject to any disclaimer, the term of this patent is extended or adjusted under 35 U.S.C. 154(b) by 251 days.

(21) Appl. No.: 14/929,079

(22) Filed: Oct. 30, 2015

(65) Prior Publication Data

US 2016/0122818 A1    May 5, 2016

(30) Foreign Application Priority Data

Oct. 31, 2014 (EP) .................................. 14191367

(51) Int. Cl.
| | | |
|---|---|---|
| C12Q 1/68 | (2018.01) | |
| C12P 19/34 | (2006.01) | |
| C12N 15/10 | (2006.01) | |
| C12Q 1/6806 | (2018.01) | |

(52) U.S. Cl.
CPC ....... *C12N 15/1065* (2013.01); *C12Q 1/6806* (2013.01)

(58) Field of Classification Search
None
See application file for complete search history.

(56) References Cited

U.S. PATENT DOCUMENTS

| | | |
|---|---|---|
| 2006/0141498 A1 | 6/2006 | Wu et al. |
| 2007/0281313 A1 | 12/2007 | Taniguchi et al. |
| 2012/0283145 A1* | 11/2012 | Wang .................... C12N 15/65 506/26 |

(Continued)

OTHER PUBLICATIONS

Extended European Search Report dated Mar. 9, 2016 for European Application No. 15192602.9, 7 pages.

(Continued)

*Primary Examiner* — Young J Kim
(74) *Attorney, Agent, or Firm* — Knobbe Martens Olson & Bear LLP (57) ABSTRACT

The present invention is directed to methods and kits for gene analysis. The methods of the invention comprise the steps of providing nucleic acid; synthesis of a single-stranded DNA that is complementary to said nucleic acid molecule by contacting the nucleic acid with a DNA polymerase, a primer and a mixture of dNTPs under conditions that allow the generation of the DNA, wherein the primer comprises a target-complementary region and wherein the dNTP mixture comprises dATP, dGTP, dCTP, dTTP and dUTP; cleaving the DNA 5' to dU sites by (i) contacting the DNA with an uracil deglycosylase to generate a basic sites at positions of dUTP incorporation in the DNA; and (ii) contacting the DNA with an apurinic/apyrimidinic (AP) endonuclease; contacting the DNA comprising at its 5'-end the nucleotide sequence of the primer with a ssDNA ligase to circularize the DNA; and sequencing the circularized cDNA. The kits comprise the components necessary to perform the methods of the invention.

13 Claims, 3 Drawing Sheets

Specification includes a Sequence Listing.

(56) References Cited

U.S. PATENT DOCUMENTS

2013/0164757 A1    6/2013    Mizuno et al.

OTHER PUBLICATIONS

De Klerk et al. (2014). RNA sequencing: from tag-based profiling to resolving complete transcript structure. *Cellular and Molecular Life Sciences*, 71:3537-3551.

Esumi et al. (2008). Method for single-cell microarray analysis and application to gene-expression profiling of GABAergic neuron progenitors. *Neuroscience Research*, 60(4):439-451.

Fullwood et al. (2009). Next-generation DNA sequencing of paired-end tags (PET) for transcriptome and genome analyses. *Genome Research*, 19:521-532.

Henson et al. (2012). Next-generation sequencing and large genome assemblies, *Pharmacogenomics*, 13(8):901-915.

Kurimoto et al. (2006). An improved single-cell cDNA amplification method for efficient high-density oligonucleotide microarray analysis. *Nucleic Acids Research*, 34(5):e42.

Liu et al. (2012). Comparison of next-generation sequencing systems. *Journal of Biomedicine and Biotechnology*, Article ID 251364, 11 pages.

Mardis, E. R. (2008). The impact of next-generation sequencing technology on genetics. *Trends in Genetics*, 24(3):133-141.

Ronaghi, M. (2001). Pyrosequencing sheds light on DNA sequencing. *Genome Research*, 11:3-11.

Rothberg et al. (2011). An Integrated semiconductor device enabling non-optical genome sequencing. *Nature*, 475:348-352.

Ruan, X., & Ruan, Y. (2012). Genome wide full-length transcript analysis using 5' and 3' paired-end-tag next generation sequencing (RNA-PET). In Ales Vancura (Ed.), *Transcriptional Regulation: Methods and Protocols* (pp. 535-562). New York: Humana Press.

Sanger et al. (1977). DNA sequencing with chain-terminating inhibitors. *Proc. Natl. Acad. Sci.*, 74(12):5463-5467.

Extended European Search Report dated Feb. 27, 2016 for European Application No. 141913167.3 filed Oct. 31, 2014, 7 pages.

* cited by examiner

SEQUENCE LISTING

```
<160> NUMBER OF SEQ ID NOS: 5

<210> SEQ ID NO 1
<211> LENGTH: 63
<212> TYPE: DNA
<213> ORGANISM: Artificial
<220> FEATURE:
<223> OTHER INFORMATION: RT primer sequence

<400> SEQUENCE: 1
ggatcagatc ggaagagcgt cgtgtaggga aagagtgtag atctcggtgg tcgccgtatc    60
att                                                                 63

<210> SEQ ID NO 2
<211> LENGTH: 41
<212> TYPE: DNA
<213> ORGANISM: Artificial
<220> FEATURE:
<223> OTHER INFORMATION: RT primer sequence
<220> FEATURE:
<221> NAME/KEY: misc_feature
<222> LOCATION: (41)..(41)
<223> OTHER INFORMATION: n is a, c, g, or t
```

```
<400> SEQUENCE: 2
caagcagaag acggcatacg agattttttt tttttttttv n                41

<210> SEQ ID NO 3
<211> LENGTH: 23
<212> TYPE: DNA
<213> ORGANISM: Artificial
<220> FEATURE:
<223> OTHER INFORMATION: fwd primer sequence

<400> SEQUENCE: 3
caagcagaag acggcatacg aga                                    23

<210> SEQ ID NO 4
<211> LENGTH: 23
<212> TYPE: DNA
<213> ORGANISM: Artificial
<220> FEATURE:
<223> OTHER INFORMATION: rev primer sequence

<400> SEQUENCE: 4
aatgatacgg cgaccaccga gat                                    23

<210> SEQ ID NO 5
<211> LENGTH: 16
<212> TYPE: DNA
<213> ORGANISM: Artificial
<220> FEATURE:
<223> OTHER INFORMATION: complement of polyA tail

<400> SEQUENCE: 5 ttttttttt tttttv                                             16
```

GENE EXPRESSION ANALYSIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 157. In particular, this application claims the benefit of European Patent Application EP14191367, filed Oct. 31, 2014, entitled Gene Expression Analysis, the disclosure of which is incorporated by reference herein in its entirety.

REFERENCE TO SEQUENCE LISTING, TABLE OR COMPUTER PROGRAM LISTING

The present application is being filed along with a Sequence Listing in electronic format. The Sequence Listing is provided as a file entitled VIERJ9-001AUS_Sequence_Listing.TXT, created Oct. 30, 2015, which is 1.15 Kb in size. The information in the electronic format of the Sequence Listing is incorporated herein by reference in its entirety.

FIELD OF THE INVENTION

The present invention is directed to a method for determining the gene expression profile of a single cell or a cell population or the presence of nucleic acid in a sample. In particular, the invention relates to a method for preparing a DNA library from a single cell, a cell population or a sample and to a DNA library produced by this method that offers the possibility of an automatable, time and cost-saving, high throughput sequencing technique of DNA molecules without the need for prior amplification. The method provides the advantage of unbiased quantification of underrepresented nucleic acid molecules in a cell or a sample.

BACKGROUND OF THE INVENTION

There are various kinds of methods to determine a comprehensive expression profile of a cell or cell population or the presence of nucleic acid molecules in a sample, one of which is the established method of sequencing. Sequencing of nucleic acid molecules became a very important analytic technique in modern molecular biology in the recent years. The development of reliable methods for DNA sequencing has been crucial for understanding the function and control of genes and for applying many of the basic techniques of molecular biology. These methods have also become increasingly important as tools in genomic analysis and many non-research applications, such as genetic identification, forensic analysis, genetic counseling, medical diagnostics and many others.

The determination of the RNA content of a cell or a tissue via sequencing provides a method for functional analysis. In existing methodologies prior to the sequencing the expressed and isolated mRNA is reverse transcribed in vitro into cDNA molecules followed by random shearing into cDNA fragments. Those fragments are tagged with linker sequences that are used to specifically amplify these fragments via a PCR step. The library of PCR amplicons obtained as such can be sequenced via various sequencing processes, e.g. deep sequencing or next generation deep sequencing methods (See e.g. Ronaghi, M. (2001), Genome Research 11:3-11; Rothberg J M, et al. Nature 475(7356): 348-52; Mardis E R, Trends Genet. (2008), Vol. 24(3):133-41; Liu L et al., J Biomed Biotechnol (2012): 251364; Henson J. et al., Pharmacogenomics (2012), 13(8):901-15; Ruan X et al., Methods Mol Biol. (2012), 809:535-62. Fullwood M J et al., Genome Res. (2009), 19(4):521-32).

A drawback of these PCR-step-based methods is the unreliable quantification of rare DNA and mRNA/cDNA molecules, respectively. This is due to the fact that PCR amplification can introduce unevenness in coverage of individual sequences. The addition of molecular random identifiers to the generated DNA fragments at the stage of DNA synthesis or reverse transcription in case of mRNA as starting material has been shown to allow eliminating the uneven coverage bioinformatically by counting individual DNA molecules only once. However, this method relies on a high sequencing coverage, which is a cost- and time-consuming procedure.

Generally, after the DNA polymerase reaction unincorporated primers have to be removed from the sample before sequencing, since otherwise the primers will dominate the sequencing reads and thereby reduce effective sequencing coverage of cDNA molecules. Typically, this is achieved by size dependent separation of the molecules, e.g. via polyacrylamide gel electrophoresis (PAGE), which suffers from poor quantitative yield and poor discrimination between molecules of similar sizes.

Hence, there is need for methods that allow improved gene expression analysis and overcome at least some of the above-mentioned drawbacks of existing technologies.

SUMMARY OF THE INVENTION

It is an object of the present invention to meet the above need by providing methods and kits to produce DNA libraries, which can directly be sequenced without prior amplification and which offer accurate determination of nucleic acid molecules even at low sequencing density. The inventors surprisingly found that this can be achieved by incorporation of dUTP into the generated DNA, cleavage at said sites of U incorporation, cyclization of the cleaved DNA fragments and subsequent sequencing thereof.

In one aspect, the invention is thus directed to a method for gene analysis, preferably gene expression profiling comprising:

a) providing nucleic acid;

b) transcribing the nucleic acid to form single-stranded DNA by contacting the nucleic acid with a DNA polymerase, a primer and a mixture of dNTPs under conditions that allow the generation of the DNA, wherein the primer comprises a target-complementary region and wherein the dNTP mixture comprises dATP, dGTP, dCTP, dTTP and dUTP, wherein the molar concentration of dUTP is about 0.01 to 20%, preferably 0.5 to 5%, of the molar concentration of dTTP, and wherein the amounts of dATP, dGTP, dCTP and (dTTP+dUTP) are essentially equimolar;

c) cleaving the DNA 5' to dU sites by (i) contacting the DNA with an Uracil Deglycosylase to generate abasic sites at positions of dUTP incorporation in the DNA; and (ii) contacting the DNA with an apurinic/apyrimidinic (AP) endonuclease;

d) optionally purifying the DNA comprising at its 5'-end the nucleotide sequence of the primer;

e) contacting the DNA comprising at its 5'-end the nucleotide sequence of the primer with a ssDNA ligase to circularize the DNA comprising at its 5'-end the nucleotide sequence of the primer; and f) sequencing the circularized DNA.

In one embodiment of the foregoing method, the nucleic acid of process a) is provided in form of a sample and is selected from genomic DNA and or cellular RNA. In some aspects of this embodiment, the RNA is mRNA, preferably eukaryotic mRNA. For example, in some embodiments, the eukaryotic mRNA may comprise a plurality of different mRNAs, and, in some embodiments the eukaryotic mRNA preferably comprises the complete cellular mRNA population. In some further embodiments:

(i) in process b) the mRNA is reverse transcribed to form single-stranded cDNA by contacting the mRNA with a RNA-dependent DNA polymerase, preferably reverse transcriptase (RT), a universal RT primer and a mixture of dNTPs under conditions that allow the generation of the cDNA, wherein the universal RT primer comprises at its 3'-end a target-complementary region comprising or consisting of a poly(dT)-dV-3'OH or poly(dT)-dV-dN-3'OH sequence to facilitate hybridization to the polyadenylation sequence of the mRNA, wherein the poly(dT) sequence is 5 to 50 nucleotides in length and V is A, C or G and N is A, C, G or T; and/or (ii) optionally, the method additionally comprises the process of digesting the mRNA contacting it with an RNAse at any time prior to process e).

In some embodiments of any of the foregoing methods, the primer comprises a 3' target-complementary region and at its 5'-end any one or more target non-complementary regions selected from the group consisting of: a unique identifier (barcode) sequence, a sequencing primer binding site and optionally one or more sequencing adapter sites, a 5' mono-phosphorylation or 5'-adenylation, a detectable label, preferably a fluorescent label, and a non-base spacer; preferably at least a unique identifier sequence and a sequencing primer binding site.

In other embodiments of any of the foregoing methods, the primer is an universal RT primer, preferably 5'-monophosphorylated, and comprises in 3' to 5' orientation either (a) a target-complementary region, preferably a poly(dT) sequence, a sequencing adapter, optionally a blocking spacer, optionally a detectable label, optionally a second sequencing adapter, a sequencing primer binding-site, and an identifier barcode sequence or (b) a target-complementary region, preferably a poly(dT) sequence, an identifier barcode sequence, a sequencing primer binding-site, a sequencing adapter, optionally a blocking spacer, optionally a detectable label, and optionally a second sequencing adapter.

In further embodiments of any of the foregoing methods, the method further comprises the process of blocking the 3' ends of non-extended primer molecules and the generated DNA molecules by use of a terminal desoxynucleotidyl transferase (TdT) in the presence of at least one di-desoxy nucleotide triphosphate (ddNTP), preferably ddTTP, wherein said process is performed after process b) and prior to process c).

In some embodiments of any of the foregoing methods, the method further comprises the process of quantifying the circularized DNA prior to the sequencing process f).

In other embodiments of any of the foregoing methods, the method further comprises the process of degrading linear DNA by contacting the DNA with an exonuclease prior to the sequencing process and the optional quantifying process.

In further embodiments of any of the foregoing methods processes a) and b) are performed tore plurality of different nucleic acid or mRNA populations, wherein for each population a universal (RT) primer with a different unique identifier sequence is used, wherein the thus generated plurality of DNA molecules is then combined for all subsequent method processes.

In other embodiments of any of the foregoing methods, process d) comprises precipitation, chromatography, column purification, and/or gel electrophoresis.

In some embodiments of any of the foregoing methods, process a) comprises isolating the nucleic acid from a sample.

In another aspect, the present invention is directed to a kit for gene analysis, preferably gene expression profiling, comprising (A) DNA polymerase;

(B) one or more primers comprising a target-complementary region (C) dNTPs, comprising dATP, dGTP, dCTP, dTTP and dUTP, optionally in form of a mixture, wherein the molar concentration of dUTP is about 0.01 to 20%, preferably 0.5 to 5%, of the molar concentration of dTTP, and wherein the amounts of dATP, dGTP, dCTP and (dTTP+dUTP) are essentially equimolar;

(D) Uracil Deglycosylase (UDG);

(E) apurinic/apyrimidinic (AP) endonuclease; and (F) ssDNA ligase.

In some embodiments, the kit further comprises:

(G) a terminal desoxynucleotidyl transferase (TdT) and at least one di-desoxy nucleotide triphosphate (ddNTP), preferably ddTTP; and/or (F) an exonuclease; and/or (H) sequencing primers.

BRIEF DESCRIPTION OF THE DRAWINGS

The invention will be better understood with reference to the detailed description when considered in conjunction with the non-limiting examples and the accompanying drawings.

FIG. 1 schematically illustrates the steps for producing a circularized cDNA library according to the described methods. In a first step reverse transcription of isolated mRNA into cDNA using the Moloney Murine Leukemia Virus (MMLV) reverse transcriptase is carried out. The primer is an RT primer and is phosphorylated at its 5' end, contains deep sequencing-specific adapters, comprises the degenerated base sequence V or VN at its 3' end (SEQ ID NO: 5) to prime the reverse transcription preferentially at the transition point between mRNA and poly-A tail, and a unique barcode sequence. dUTP is added to the dNTP mixture at a final concentration of 1-100 µM. In a second (optional) step mRNA is digested using RNAseH and a 3'-end blocking of cDNA and unincorporated primers using TdT (terminal desoxynucleotidyl transferase) and di-desoxy-TTP, which prevents blocked molecules from circularization and thus from sequencing, is carried out. In the next step, the cDNA molecules are site-specifically cleaved by adding uracil deglycosylase to generate abasic sites at positions of dUTP incorporation and apurinic/apyrimidinic (AP) endonuclease (APEi) is added to cleave the cDNA 5' to abasic sites, leaving 3'OH ends DNA molecule purification is then achieved by silica column or precipitation to remove nucleotides which inhibit circularization and the circularization reaction is carried out using a ssDNA ligase (e.g., CircLigase® (Epicentre)) and ATP. Optionally, linear DNA is removed by exonuclease (Exonuclease I® (NEB)) treatment. Subsequently the optional step of quantification using quantitative PCR wherein primers that only amplify circularized cDNA molecules are used can be carried out and a standard dilution series of a linear control template may be used to allow absolute quantification.

DETAILED DESCRIPTION OF THE INVENTION

The present invention is directed to a method of gene expression profiling and identification of nucleic acid in a sample.

"Gene expression", as used herein, relates to a process in which information from a gene is used for the synthesis of a gene product. In cell-based expression systems the expression comprises transcription and translation steps.

The term "gene expression profiling", as used herein, refers to method(s) for determining the mRNA expression profile of a given cell or a population of cells at a given time under a given set of conditions.

The invention is based on the inventors' finding that a library of circular DNA molecules for high-throughput deep sequencing procedures can be produced by a method that employs synthesis of a single stranded DNA complementary to a nucleic acid molecule of interest by using DNA polymerase that introduces defined cleavage sites into the DNA molecules, subsequent site-specific cleavage of the DNA and circularization of the DNA fragments.

The term "DNA" as used herein refers to any type of DNA molecules and also includes cDNA.

The term "cDNA", as used herein, refers to single-stranded complementary DNA that is reverse transcribed from mRNA and is therefore a copy of the intron-free active RNA.

The method of the invention can be performed without prior amplification and optionally also without purification after DNA synthesis reaction, typically a reverse transcription reaction.

The term "amplification" as used herein, refers to a process by which extra or multiple copies of a particular polynucleotide are formed. Amplification includes methods such as LCR, ligation amplification (or ligase chain reaction. LCR) and amplification methods.

The term "reverse transcription", means a method wherein a cDNA copy of an mRNA molecule is synthesized. By reverse transcribing the mRNA population of a given cell or cell population, a cDNA library may be established.

"cDNA library", as used herein, refers to a collection of cDNAs representing the mRNAs expressed in a cell or cell population.

The term "cell population" refers to a grouping of cells isolated from a tissue or from a cell culture.

The term "mRNA", as used herein, refers to messenger RNA which is a transcription product of a gene expression process.

In a first aspect, the invention is thus directed to a method for gene analysis, preferably gene expression profiling, comprising:
a) providing nucleic acid;
b) transcribing the nucleic acid to form single-stranded DNA by contacting the nucleic acid with a DNA polymerase, a primer and a mixture of dNTPs under conditions that allow the generation of the DNA, wherein the primer comprises a target-complementary region and wherein the dNTP mixture comprises dATP, dGTP, dCTP, dTTP and dUTP, wherein the mar concentration of dUTP is about 0.01 to 20%, preferably 0.5 to 5%, of the molar concentration of dTTP, and wherein the amounts of dATP, dGTP, dCTP and (dTTP+dUTP) are essentially equimolar;
c) cleaving the DNA 5' to dU sites by (i) contacting the DNA with an Uracil Deglycosylase to generate abasic sites at positions of dUTP incorporation in the DNA; and (ii) contacting the DNA with an apurinic/apyrimidinic (AP) endonuclease;
d) optionally purifying the DNA;
e) contacting the DNA with a ssDNA ligase to circularize the DNA; and
f) sequencing the circularized DNA.

The DNA purified in step d) and the DNA contacted with a ssDNA ligase in step e) of the method for gene analysis comprises the most 5' DNA fragment that resulted from the digestion of the single-stranded DNA with the apurinic/apyrimidinic (AP) endonuclease. This 5' DNA fragment has a nucleic acid sequence that is identical to the nucleic acid sequence of the primer and comprises the complementary region of the primer as well as the non-complementary regions of the primer. These non-complementary regions include, but are not limited to a unique identifier (barcode) sequence, a sequencing primer binding site and optionally one or more sequencing adapter sites, a 5' mono-phosphorylation or 5'-adenylation, a detectable label, preferably a fluorescent label, and a non-base spacer; preferably at least a unique identifier sequence and a sequencing primer binding site. Therefore, the DNA purified in step d) and the DNA contacted with a ssDNA ligase in step e) of the method for gene analysis comprises at its 5'-end the nucleotide sequence of the primer.

In the described methods, the nucleic acid can be provided by any means known in the art. Typically it is preferred in form of a sample. Said sample may be any type of cell- or nucleic acid-containing sample and may be a biological sample, such as a cellular or tissue sample, a body fluid sample, such as a blood sample, or a feces sample. In other various embodiments, the sample may be a food sample, an environmental sample, a forensic sample or a mold culture. The samples may be used as collected or may be subjected to various processing steps, such as purification and/or enrichment, before being used in the methods described herein.

The nucleic acid molecules that are analyzed can be any type of RNA, such as mRNA but also any non-coding RNA, such as rRNA, tRNA, asRNA, hnRNA, miRNA, ribozymes, siRNA, snoRNA, or snRNA. In various other embodiments, the nucleic acid analyzed is DNA, preferably genomic DNA. In preferred embodiments, the nucleic acid is genomic DNA or mRNA.

The nucleic acid may generally be of prokaryotic or eukaryotic. However, nucleic acids, such as genomic DNA or mRNA of eukaryotic origin are preferred.

While reference is generally made to "nucleic acid" herein, it should be understood that this term includes single nucleic acid molecules as well as mixtures of different nucleic acid molecules. For example, it can be genomic DNA or a pool of RNA molecules, in particular mRNA molecules, isolated from a cellular or tissue sample or any other sample type comprising cells, genomic DNA or RNA, in particular mRNA molecules, including body fluids.

In preferred embodiments of the invention, but without limitation, the nucleic acid molecules are eukaryotic mRNAs. Providing the mRNA may comprise isolating the mRNA from a eukaryotic cell sample. it is preferred that the mRNA comprises a multitude of different mRNA molecules, for example the mRNA population of a given cell, cell type or cell line. Methods for the isolation of RNA molecules from such samples are known in the art and kits for such mRNA isolation are commercially available.

In some embodiments, mRNA can be released from the cells by lysing the cells. Lysis can be achieved by, for example, heating the cells, or by the use of detergents or other chemical methods, or by a combination of these. However, any suitable lysis method known in the art can be used. A mild lysis procedure can advantageously be used to prevent the release of nuclear chromatin, thereby avoiding genomic contamination of the cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in FOR buffer II (Applied Biosystems) supplemented with 0.5% NP-40 (Kurimoto et al., Nucleic Acids Res 34(5):e42 (2006)), Lysis can also be achieved with a protease such as Proteinase K or by the use of chaotropic salts such as guanidine isothiocyanate (See, e.g., U.S. Publication No. 2007/0281313).

Eukaryotic mRNA derived from cells typically comprises a plurality of different mRNA molecules and in some embodiments comprises the complete cellular mRNA population. Accordingly, the steps of providing the eukaryotic mRNA and reverse transcribing the mRNA may be performed for a plurality of different mRNAs or mRNA populations, wherein for each mRNA/mRNA population a universal RT primer with a different unique identifier sequence is used, wherein the thus generated plurality of cDNA molecules is then combined for all subsequent method steps. By using primers with different unique identifier sequences for the reverse transcription procedure, also mRNA populations derived from different sources may be combined in all subsequent steps, while still being identifiable and distinguishable.

In the step of single stranded DNA synthesis a DNA polymerase is used. In case the analyzed nucleic acid is RNA a RNA-dependent DNA polymerase or a DNA polymerase that can use DNA as well as RNA as a template may be used. For reverse transcribing mRNA to form single-stranded cDNA, preferably reverse transcriptase (RT) is used.

Synthesis of cDNA from mRNA in the methods described herein can be performed directly on cell lysates or other sample types. In such embodiments, the reaction mix for reverse transcription is added directly to the sample. Alternatively and more preferably, the mRNA can be isolated from the sample and/or purified. This can help to reduce mitochondrial and ribosomal contamination. mRNA purification can be achieved by any method known in the art, for example, by binding the mRNA to a solid phase. Commonly used purification methods include paramagnetic beads (e.g. Dynabeads). Alternatively, specific contaminants, such as ribosomal RNA can be selectively removed using affinity purification.

In various embodiments, the reverse transcriptase (RT) is selected from the group consisting of MMLV RT, Avian Myeloblastosis Virus (AMV) RT, Rous Sarcoma Virus (RSV) RT, Human Immunodeficiency Virus (HIV) RT, Equine Infectous Anemia Virus (EIAV) RT, Rous associated Virus-2 (RAV2) RT, Avian Sarcoma Leukosis Virus (ASLV) RI, Maxima RT (Thermo Scientific), and RNaseH (−) RT, such as Maxima H minus RT (Thermo Scientific), SuperScript® RT, SuperScript® II RT, SuperScript® III RT and ThermoScript™ RT (Life Technologies). The RT may be provided and used in a buffer suitable for the reverse transcription reaction.

In various alternative embodiments, a DNA polymerase with reverse transcriptase activity, like *Thermus thermophilus* HB-8 (Rh) DNA polymerase, is used. In yet alternative embodiments, a DNA-dependent DNA polymerase can be used to amplify DNA as the initial nucleic acid species to be analyzed. The DNA-dependent DNA polymerase can be selected from the group consisting of Tag polymerase (*Thermus aquaticus*) and Phusion-U polymerase (Thermo Fisher). The polymerase may be provided and used in a buffer suitable for the polymerase reaction. Linear amplification can be achieved by repeatedly heating and cooling the reaction to 95° C. and 68-72° C. or 95°, 60°, and 68-72°.

For transcribing the nucleic acid of interest into a complementary single-stranded DNA molecule, primers are used. To allow this, the primers used comprise a target-complementary region. This target-complementary region facilitates hybridization to the nucleic acid sequence under the synthesis conditions and allows elongation of the primer by the DNA polymerase. The target-complementary regions of the utilized primers typically are between 5 and 50 nucleotides in length. The length and sequence of said target-complementary region is selected such that the desired hybridization specificity under the given synthesis conditions is achieved.

The term "hybridization", as used herein, refers to the annealing process of a primer to a complementary sequence of a nucleic acid molecule.

In various preferred embodiments, the target-complementary region is located at the 3'-end of the primer to allow elongation. The 5'-end of such primers may comprise any one or more of a variety of target non-complementary regions that provide for different functionalities and include, without limitation, a unique identifier (barcode) sequence; a sequencing primer binding site and optionally one or more sequencing adapter sites; a 5' mono-phosphorylation or 5'-adenylation; a detectable label, preferably a fluorescent label; and a non-base spacer.

In various preferred embodiments, the primer comprises at its 3'-end the target-complementary region and a sequencing primer binding site 5' to the target-complementary region. Depending on the sequencing method employed, the primer may comprise one or more, typically two, sequencing adapter sites. These are in various embodiments located between the sequencing primer binding site and the target-complementary region. The location of the sequencing primer binding site 5' to the target complementary region ensures that after circularization, in the following sequencing step the newly synthesized (typically reverse transcribed) sequence is sequenced first. Further, the location of two sequencing adapter sites between the target complementary region and the sequencing primer binding site ensures that the to-be-sequenced part of the elongated and circularized primer is located between the two adapter sites. This is to be considered when designing the primer and deciding on orientation of the adapter sites.

The sequencing primer binding site is a sequence that is complementary to the sequence of the primer used for sequencing and designed such that it allows hybridization under sequencing conditions.

The term "sequencing adapter". as used herein, refers to a nucleic acid sequence that can specifically bind to oligo sequences or complementary adapters that are specific for the used sequencing system and, for example, facilitate capture onto a solid support or particle. The sequencing adapters may be sequencing technology-specific, i.e. if the Illumina sequencing protocol is to be used for the sequencing step, the sequencing adapters are Illumina adapters.

The terms "elongated primer", "extended primer" or "(synthesized) DNA molecule", as interchangeably used herein, refer to the primer after the DNA synthesis (transcription; elongation) and optionally also after site-specific cleavage.

To allow identification, it is further preferred that the primer comprises a unique identifier sequence (barcode sequence). This is typically located adjacent to the sequencing primer binding-site. This sequence can be any sequence that is suitable and sufficient to allow identification. Suitable sequences are known in the art. in any case, the identifier sequence is selected such that it does not interfere with any following enzymatic treatment, hybridization and/or sequencing step/event. In certain embodiments, the barcode comprises a sequence of about 4 to about 50 nucleotides, of about 4 to about 25 nucleotides, of about 4 to about 20 nucleotides, of about 4 to about 15 nucleotides, of about 8 to about 12 nucleotides, or about 3, 4, 5, 6, 7, 8, 9, 10, 11, 12, 13, 14, 15, 16, 17, 18, 19, or 20 nucleotides. In certain embodiments, the barcode sequences used are generated by a pseudo-random sequence generator.

The primer may further comprise a mono-phosphorylation or an adenylation at its 5' end. The 5'-mono-phosphorylation or adenylation facilitates the circularization of the elongated primer by ssDNA ligase, as in the step of DNA circularization the 5' end of the elongated primer is ligated to the 3' end of the transcribed DNA sequence.

Alternatively, the primer may be enzymatically phosphorylated after elongation and before the circularization. Phosphorylation can, for example, be achieved by use of a polynucleotide kinase.

In various embodiments, the primer can further comprise a detectable label, preferably a fluorescent label. However, the label is not limited to fluorescent labels but can also be any other nucleic acid-compatible label known in the art. The label may facilitate detection or quantification of the primer or the generated cDNA molecules.

In still further embodiments, the primer may comprise a non-base spacer, which can be any non-nucleotide spacer known in the art, e.g. a carbon spacer that functions as an effective blocking agent against polymerase extension. Exemplary spacers can be, without limitation, hexa-ethyleneglycol spacers, tri-ethyleneglycol spacers, C3 spacers, 1',2'-dideoxyribose spacers, or photo-cleavable spacers. The function of the spacer is to hinder unwanted circular amplification of the cDNA in the later sequencing process, e.g. during cluster generation on an Illumine flowcell.

In preferred embodiments of the invention, the universal RT primer comprises in 3' to 5' orientation the target-complementary region, a sequencing adapter, an optional non-base blocking spacer, an optional label, an optional second sequencing adapter, a sequencing primer binding-site, and an identifier barcode sequence. In other embodiments of the invention, the universal RT primer comprises in 3' to 5' orientation a target-complementary sequence, an identifier barcode sequence, a sequencing primer binding-site, a sequencing adapter, an optional non-base blocking spacer, an optional label, and an optional second sequencing adapter.

The concrete primer sequence will depend on the target nucleic acid. However, it may in various embodiments be preferable to use a universal primer that hybridizes to a multitude of different target molecules which are then later identified by sequencing. "Universal primer", as used herein, thus relates to a primer that is not specific for a single target sequence, but rather indiscriminately binds to two or more different target sequences, typically a large population of different targets. This is usually achieved by either randomizing the universal primer target-complementary region sequence or by using a target-complementary sequence that recognizes a sequence element present in a multitude of different target molecules, such as a common sequence motif.

A randomized sequence may be a poly(dN) or $(dN)_{6-10}$ sequence, wherein N is A, G, T or C.

A universal target-complementary region that hybridizes to all the poly-A tail present in all eukaryotic mRNA molecules is a poly(dT) sequence.

Consequently, in preferred embodiments where the nucleic acid of interest is a eukaryotic mRNA, the primer is a universal RT primer that under condition of a reverse transcriptase enzymatic activity acts as a starting point for template-directed cDNA synthesis. Such a primer may comprise at its 3'-end a target-complementary region comprising or consisting of a poly(dT)-dV-3'OH or poly(dT)-dV-dN-3'OH sequence to facilitate hybridization to the polyadenylation sequence of the mRNA, wherein the poly(dT) sequence is 5 to 50 nucleotides in length and V is A, C or G and N is A, C, G or T. The V or VN sequence at its 3'-end is a degenerate sequence, i.e. the RT primer includes a population of primers that differ in this position in that they have either an A, C or G nucleotide for V and, if present, any one of A, G, C or T for N, This allows recognition of the end of the poly-A tail of the mRNA molecule and recognition of the 3'-end of the gene-specific mRNA region, which in turn ensures that reverse transcription of the gene-specific mRNA sequence is correctly initiated. As already described above, the poly(dT) sequence should be long enough to allow specific hybridization to the poly-A tail of the mRNA molecules. Typically, the length of the poly(dT) sequence is thus 10 to 30, preferably 15 to 25 T nucleotides.

The dNTP mixture used for the reverse transcription step comprises dATP, dGTP, dCTP, dTTP and dUTP. In said mixture, the molar concentration of dUTP is about 0.01 to 20%, preferably 0.5 to 5%, of the molar concentration of dTTP. Generally, the amounts of dATP, dGTP, dCTP and (dTTP+dUTP) are essentially equimolar, which means that the combined amount of dTTP and dUTP is about the same as the amount of each of dATP, dGTP and dCTP, respectively. "Essentially equimolar", as used in this context, means that the respective nucleotides or nucleotide combinations are used in nearly identical amounts. In various embodiments, "essentially equimolar" means that the variance in the concentrations of the nucleotides in the mixture is no more than about ±5%.

As already described above, only the provision of the nucleic acid molecule, i.e. typically its isolation, and DNA synthesis have to be performed for individual samples, with these steps being easily automatable. All subsequent steps can then be performed on a pool of elongated primer molecules from different samples. In order to facilitate pooling of a multitude of samples, the universal primer used for each sample may comprise a unique identifier (barcode) sequence. This sequence allows identification of each DNA population generated by use of a given primer and thus serves as an identification means for the origin of the DNA, i.e., the sample it is derived from, even in case the DNA from multiple samples has been combined for sequencing analysis.

In embodiments where the nucleic acid is (eukaryotic) mRNA, the mRNA may digested once the cDNA has been synthesized, i.e., prior to step c) and/or d) and/or e). The digestion step may be carried out by contacting the mRNA molecules with a ribonuclease (commonly abbreviated RNase), which catalyzes the degradation of the RNA molecules into smaller fragments, in particular single nucleotides. As the RNase is RNA-specific, the cDNA molecules are unaffected by this treatment and stay intact. This way, the mRNA molecules do not interfere with the following sequencing reaction. In various embodiments of the invention, the RNAse may be selected from the group consisting of RNAse A, RNAse H, RNAse I, RNAse T and RNAse activity of any Reverse Transcriptase. Alternatively, mRNA can be degraded by addition of NaOH and heating.

In various embodiments of the invention, the method further comprises the step of blocking the 3' ends of non-extended primer molecules and the generated DNA molecules by use of a terminal desoxynucleotidyl transferase (TdT) in the presence of at least one di-desoxy nucleotide triphosphate (ddNTP), preferably ddTTP, wherein said step is performed after reverse transcription and prior to cleaving the DNA 5' to abasic sites. The TdT enzyme used may be from calf, human, or recombinant source. Blocking the 3' ends of the non-extended primers and the DNA molecules prevents circularization of said molecules, unless they are intramolecularly cleaved at UDG-generated abasic sites by AP endonucleases action thus providing a 3' OH end group to the DNA fragment. The non-circularized, linear molecules will then either fail to be sequenced or can then be more easily be degraded or separated from the circular DNA molecules before the subsequent sequencing step. The term "non-extended primer", as used herein, refers to a primer that either does not hybridize to the target or is not elongated after hybridizing to a template nucleic acid molecule and thus does not contain any useful sequence information.

Site-specific cleavage of the DNA molecules is achieved by first generating abasic sites in the DNA molecules by adding uracil deglycosylase (UDG) to the DNA. Said enzyme cleaves the base uracil at one or more positions within the DNA molecule where dUTP has been incorporated, thus generating abasic sites at these positions. In one specific embodiment, the uracil deglycosylase (UDG) is an *E. coli* UDG. Subsequently, an apurinic/apyrimidinic (AP) endonuclease is added that cleaves the DNA 5' to the abasic sites, leaving 3'OH ends. As the dUTP is randomly integrated into the nascent DNA during reverse transcription, the UDG and AP endonuclease treatment generates a population of truncated DNA molecules of varying length. The average length of said fragments can be controlled by the amount of dUTP used during reverse transcription, in particular the dUTP:dTTP ratio. The less dUTP is used, the longer the fragments are and vice versa. The concentration of dUTP and as a result the length of the DNA should be controlled such that specific identification of the genes after sequencing is possible. By using this method, the DNA fragment size is not dependent on reaction time or other critical parameters, which allows a much higher throughput when sequencing RNA or DNA from different samples. Furthermore, the endonuclease mediated cleavage at dUTP sites gives rise to 3' OH ends which are necessary for the following circularization reaction to fuse with the monophosphorylated or adenylated 5' ends.

In various embodiments, the apurinic/apyrimidinic (AP) Endonuclease is selected from the group consisting of APE1 (optionally from *HOMO sapiens*). Endonuclease III®, T4 Endonuclease® V. Endonuclease IV®, preferably APE1 (all available from New England Biolabs).

The following optional step of purifying the DNA molecules from RNA molecules, enzymes, unused primers or any degradation products of the aforementioned components can be performed by any nucleic acid purification method known in the art. Suitable techniques involve, without limitation, precipitation, centrifugation, chromatography (affinity or size exclusion), silica column purification, electrophoretic techniques, such as gel electrophoresis, and the like. In various embodiments of the invention, the DNA purification comprises precipitation, chromatography, and/or gel electrophoresis.

The purified DNA molecules are then circularized by contacting the DNA with a single-stranded DNA ligase (ssDNA ligase), which fuses the 3'OH end to the monophosphorylated or adenylated 5' end of the DNA molecule. The single-stranded DNA ligase (ssDNA ligase) may be selected from the group consisting of CircLigase (Epicentre) and T4 RNA ligase I/II® (New England Biolabs), preferably is CircLigase® (Epicentre).

In some embodiments, gel electrophoresis is used to separate circularized DNA from linear DNA or to quantify circularized DNA, as known from prior art, wherein the gel can be made of a variety of gel matrix materials, including polyacrylamide, agarose, polyacrylamide-agarose composites, and the like.

In other embodiments, the circularized DNA molecules are purified by using commonly known precipitation methods, such as ethanol precipitation, precipitation by isopropanol, polyethylene glycol in aqueous sodium chloride or spin column-based solid phase extraction.

In various embodiments, the circularized DNA molecules are purified by chromatography, which refers to a process in which a chemical mixture carried by a liquid or gas is separated into components as a result of differential distribution of the chemical entities as they flow around or over a stationary liquid or solid phase.

In various embodiments, the invention further comprises the step of quantifying the circularized DNA prior to the sequencing step. The quantifying may comprise quantitative PCR (qPCR) or digital PCR (dPCR), optionally using primers capable of only amplifying circular DNA end/or a linear control template for absolute quantification.

In various embodiments the method further comprises the step of degrading linear DNA by contacting the DNA with an exonuclease after the circularization step but prior to the sequencing step and optionally the quantifying step. In various embodiments, the exonuclease may be selected from the group consisting of phosphodiesterase, nuclease, exonuclease I, exonuclease VII, an exonuclease activity of *E.* coli DNA polymerase an exonuclease activity of a Klenow fragment of DNA polymerase I, an exonuclease activity of T4 DNA Polymerase® (NEB), an exonuclease activity of T7 DNA Polymerase® (NEB), an exonuclease activity of Taq DNA Polymerase® (Roche, NEB, Qiagen or Life Technologies), an exonuclease activity of Deep Vent® DNA polymerase (NEB), and an exonuclease activity of Ventr® DNA polymerase (NEB).

In various embodiments of the invention, a polymerase chain reaction (PCR) is performed before sequencing to increase the amount of material to be sequenced. The PCR primers used for said amplification may bind to the sequencing adapter sequences of the circular cDNA or to sequence portions of the cDNA originating from known sequences in the original nucleic acid species. This can be important if the initial amount of RNA is limited, because it was derived from a single cell.

In various embodiments of the invention, the sequencing is deep sequencing, preferably next generation deep sequencing.

The circularized DNA molecule is then sequenced. For sequencing, any sequencing reaction known in the art can be used. The term "sequencing", as used herein, generally means a process for determining the order of nucleotides in a nucleic acid, "Sequencing", as used herein, comprises de novo identification of unknown sequences as well as identification of known sequences or sequence changes, e.g. mutations. A variety of methods for sequencing nucleic acids is well known in the art. Such sequencing methods include the Sanger method of dideoxy-mediated chain termination as described, for example, in Sanger et al., Proc. Natl. Acad. SOL 74:5463 (1977) or next generation sequencing or higher generation sequencing.

The term "next generation sequencing", as used herein, refers to sequencing technologies having increased throughput as compared to traditional Sanger- and capillary electrophoresis-based approaches, for example with the ability to generate hundreds of thousands or millions of relatively short sequence reads at a time. Some examples of next generation sequencing techniques include, but are not limited to, sequencing by synthesis, sequencing by ligation, and sequencing by hybridization. Examples of next generations sequencing methods include pyrosequencing as used by the GS junior and GS FLX Systems (454 Life Sciences), sequencing by synthesis as used by Illumina's Miseq and Solexa system, the SOLiD™ (Sequencing by Oligonucleotide Ligation and Detection) system (Life Technologies inc.), and ion Torrent Sequencing systems such as the Personal Genome Machine or the Proton Sequencer (Life Technologies Inc), and nanopore sequencing systems (Oxford nanopore).

The term "deep sequencing", as used herein, refers to nucleic acid sequencing to a depth that allows each base to be read multiple times from independent nucleic acid molecules (e.g., a large number of template molecules is sequenced relative to the length of the sequence) and allows sequencing of thousands of molecules simultaneously, thereby allowing to characterize complex pools of nucleic acid molecules and increasing sequencing accuracy. Deep sequencing of the transcriptome, also known as RNA-Seq, provides both the sequence and frequency of contained RNA molecule species that are present at any particular time in a specific cell type, tissue or organ.

In another aspect, the present invention is directed to a kit for gene analysis, preferably gene expression profiling, comprising (A) DNA polymerase;
(B) one or more primers comprising a target-complementary region
(C) dNTPs, comprising dATP, dGTP, dCTP, dTTP and dUTP, optionally in form of a mixture, wherein the molar concentration of dUTP is about 0.01 to 20%, preferably 0.5 to 5%, of the molar concentration of dTTP, and wherein the amounts of dATP, dGTP, dCTP and (dTTP+dUTP) are essentially equimolar;
(D) uracil deglycosylase (UDG);
(E) apurinic/apyrimidinic (AP) endonuclease; and
(F) ssDNA ligase.

The kits of the invention comprise in various embodiments the reagents that allow producing DNA libraries of circular DNA molecules that can directly be used in high-throughput next generation (deep) sequencing without prior amplification.

The DNA polymerase may be a RNA-dependent DNA polymerase, in particular a reverse transcriptase, such as those disclosed above in connection with the inventive methods.

The one or more primers may each be defined as described above in connection with the inventive methods. In various embodiments, the primers are universal RT primers comprising a target-complementary region at the 3' end comprising or consisting of a poly(dT)-dV-3'OH or a poly(dT)-dV-dN-3'OH sequence, wherein the poly(dT) sequence is 5 to 50 nucleotides in length and V is A, C or G and N is A, C, G or T.

Similarly, the uracil deglycosylase (UDG), the apurinic/apyrimidinic (AP) endonucleases and/or the ssDNA ligase may be any of those disclosed above in connection with the inventive methods.

In a further embodiment, the kit further comprises a terminal desoxynucleotidyl transferase (TdT) and at least one di-desoxy nucleotide triphosphate (ddNTP), preferably ddTTP. Including such an enzyme and the ddNTP allows blocking the ends of non-extended primers and the newly synthesized DNA molecules, as described above.

In various embodiments, the kit may further comprise an exonuclease to degrade linear DNA.

In various embodiments, the kit may further comprise chemicals or means useful for DNA isolation/purification, all of which are well-known in the art.

In preferred embodiments, the kit may further comprise a ribonuclease for mRNA digestion.

In further embodiments, the kit may also comprise a linear DNA and control template primers capable of amplifying only circular DNA for qPCR quantification.

In still further embodiments, the kit may comprise sequencing primers. The term "sequencing primer", as used herein, refers to a single-stranded oligonucleotide generally with a free 3'-OH group capable of acting as a point of initiation for template-directed DNA synthesis within the sequencing reaction under suitable conditions for example, buffer and temperature, in the presence of a dNTP mixture and a polymerase. The length of the primer typically varies from 10 to 40, preferably 15 to 30 nucleotides. The primers are usually selected such that they hybridize to the respective binding site in the generated DNA molecules under sequencing conditions.

It is understood that all embodiments disclosed herein in relation to the inventive methods are, insofar possible, equally applicable to the kits of the invention and vice versa.

All documents cited are herein incorporated by reference in their entirety.

The invention is further illustrated by the following non-limiting examples.

EXAMPLES

Materials and Methods

1. Complete Protocol for Producing a Circularized cDNA Library from Eukaryotic Cells:

1.1. Total RNA was Purified from HEK 293T Cells

| | |
|---|---|
| 5 × 10⁶ | HEK 293T cells, pelleted |
| 350 μl | Buffer RLT (Qiagen) |
| 350 μl | 70% ethanol |
| Apply to silica column (CB-C250, Gentic Biosciences) | |
| Spin for 15 sec. at 10,000 g, discard flow-through | |
| 700 μl | Buffer RW1 (Qiagen) |
| Spin for 15 sec. at 10,000 g, discard flow-through | |
| 500 μl | Buffer RPE (Qiagen) |
| Spin for 15 sec. at 10,000 g, discard flow-through | |
| 500 μl | Buffer RPE (Qiagen) |
| Spin for 2 min. at 10,000 g | |
| Place column in a new 1.5 ml tube | |
| 30 μl | water |
| Spin for 1 min. at 10,000 g | |

1.2. (Optional) Possible DNA Contaminations in Isolated RNA were Removed Using a DNAseI digestion Step:

| | |
|---|---|
| 0.5 μl | DNAse buffer (10x) |
| 2 μl | HEK 293T RNA 800 ng/μl (from column-based RNA purification 1.1.) |
| 2 μl | H$_2$O |
| 0.5 μl | DNAse I (1 U/μl, Thermo scientific) |
| Incubation for 30 min at 37° C. | |
| 0.5 μl | EDTA 25 mM |
| Incubation for 10 min at 70° C. | |

13. Isolated mRNA was Transcribed into cDNA in a Reverse Transcription Step:

```
5.25 µl   DNA-free RNA (approx. 800 ng/µl)
          (from step 1.2.)

1 µl      0.5 µM RT primer dilution (optional:
          5-100 µM) synthesized by Integrated
          DNA Technologies in Ultramer
          quality: /5Phos/GGATCAGATCGGAAGAGCG
          TCGTGTAGGGAAAGAGTGTAGATCTCGGTGGTCGC
          CGTATCATT (SEQ ID NO: 1)/iSp18/CAAG
          CAGAAGACGGCATACGAGATTTTTTTTTTTTTTT
          VN(SEQ ID NO: 2)
```

Annealing for 5 min at 65° C.

| | |
|---|---|
| 2 μl | 5x RT buffer (250 mM Tris-HCl pH 8.3 at 25° C., 250 mM KCl, 20 mM MgCl2, 50 mM DTT) |
| 1 μl | dNTP mix (10 mM each of: dATP, dTTP, dGTP, dCTP, Thermo scientific) with 0.1 mM dUTP (Epicentre) |
| 0.25 μl | ribolock RNAse inhibitor (40 U/μl, Thermo scientific) |
| 0.5 μl | Maxima RNAse H minus RT ® (Thermo scientific) |
| Incubation for 1 h at 42° C. | |
| Incubation for 10 min at 70° C. | |

14. (Optional Step) in Order to Exclude Non-Extended RT Primers from Circularization. Thus Reducing Background by Empty Primer Sequencing, all 3' Ends were Blocked Using Terminal Desoxynucleotidyl Transferase (TdT) and Di-Desoxy-TTP, in the Same Reaction, mRNA was Degraded Using RNAse H

| | |
|---|---|
| 10 μl | reaction 1.3 |
| 0.5 μl | RNAse H ® (5 U/μl, Thermo scientific) |
| 1 μl | ddTTP 40 mM |
| 1 μl | TdT (15 U/μl, Thermo scientific) |
| Incubation for 1 h at 37° C. | |
| Incubation for 10 min at 70° C. | |

1.5. the cDNA was Cleaved by an Enzymatic Uracil Excision

| | |
|---|---|
| 12.5 μl | reaction 1.4 |
| 0.5 μl | UDG (1 U/μl, Thermo scientific) |
| 1 μl | APE1 ® (10 U/μl, NEB) |
| Incubation for 1 h at 37° C. | |

1.6. (Optional) any Remaining RNA was Removed Using NaOH-Based Hydrolysis

| | |
|---|---|
| 14 μl | reaction 1.5 |
| 2 μl | 1N NaOH |
| Incubation for 20 min at 70° C. | |
| 2 μl | 1M Tris pH 7.4 |

1.7. The cDNA was Purified Using Silica-Based Spin Columns

| | |
|---|---|
| 18 μl | reaction 1.6 |
| 500 μl | Binding buffer (Jena Analytik PCR purification kit) |
| Add to spin column (Jena Analytik PCR purification kit) | |
| Centrifugation for 2 min at 12,000 g | |
| Put spin column into a fresh tube | |
| add 10 μl | H$_2$O |
| Centrifugation for 1 min at 8,000 g | |
| Discard spin column | |

1.8. The Purified cDNA was Circularized Using CircLigase

| | |
|---|---|
| 7.5 μl | purified DNA eluate (concentration not measurable by OD) |
| 0.5 μl | ATP 1 mM |
| 0.5 μl | MnCl$_2$ 50 mM |
| 1 μl | 10x buffer (Epicentre) (0.5M MOPS pH 7.5, 0.1M KCl, 50 mM MgCl2, 10 mM DTT) |
| 0.5 μl | CircLigase I ® (100 U/μl, Epicentre) |
| Incubation for 3 h at 60° C. | |
| Incubation for 10 min at 80° C. | |

1.9. (Optional Step) Linear cDNA Molecules are Removed by Exonuclease I Treatment

| | |
|---|---|
| 10 μl | reaction sample 1.8 |
| 1 μl | Exonuclease I (20 U/μl, NEB) |
| Incubation for 20 min at 37° C. | |
| Incubation for 20 min at 80° C. | |
| 20 μl | H$_2$O |

1.10. The Circular cDNA was Quantified Using qPCR

```
5 µl    FastSYBR 2x mastermix (Life technologies)

0.1 µl  50 µM fwd primer (CAAGCAGAAGACGGCATACGAGA,
        IDT, SEQ ID NO: 3)
```

-continued

```
0.1 µl   50 µM rev primer (AATGATACGGCGACCACCGAGAT,
         IDT, SEQ ID NO: 4)
```

| | |
|---|---|
| 2 µl | reaction 1.9 |
| 2.8 µl | water |
| 40 cycles in an ABI 7900HT fast real-time qPCR system (Applied Biosystems) | |

1.11. the Circular DNA was Subjected to MiSeq Deep Sequencing

| | |
|---|---|
| 20 µl | reaction 1.9 |
| 20 µl | Unrelated denatured PCR products to fill up the MiSeq flowcell |
| 560 µl | Illumina Hyb buffer |

The whole solution is added into the sample well of a MiSeq-v2-300-cycle cassette The MiSeq is run according to the manufacturer's instructions using matrix-hardcoding and 250 sequencing cycles

Figure 4:
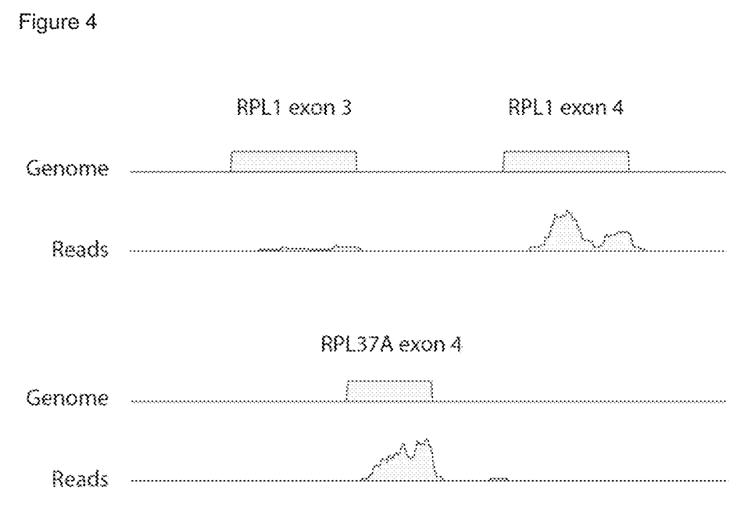
FIG. 4 shows the results of sequencing using the method for gene expression analysis of the instant invention with RNA molecules isolated from HEK 293T used as input. From a single reaction, Illumina MiSeq deep sequencing yielded more than 23000 sequencing reads mapping to the human genome, 49.9% of which aligned to annotated RefSeq genes. 4719 human genes had at least one single sequencing hit.

Example 1: Construction of a Circularized cDNA Library Using HEK 293T RNA or Water as Input According to the Method of this Invention A circularized cDNA library was generated and deep sequencing was conducted according to protocols 1.1.-1.11. The quantification of circularized DNA molecules via qPCR (protocol step 1.10.) revealed that the amount of circular cDNA was higher by factor >1000 when RNA was used as the input in comparison to water. A single lumina Miseq sequencing run yielded >23,000 sequencing reads that mapped to the human genome, 49.9% of which aligned to genes annotated by the NCBI Reference Sequence Database. FIG. 4 depicts the local read frequency at two exemplary human genes. We found alignment hits for 4719 individual human genes; this result proves that the method of this invention is functioning.

Of note, individual sequencing reads aligning to genetic loci with more than one sequencing hit randomly covered the locus instead of aligning at one or a few common positions (FIG. 4). We interpret this result as confirming that our method does not produce amplification bias, which would otherwise result in single cDNA sequences being sequenced numerous times. An advantage of using our amplification-free sequencing method is therefore that every sequencing read originates from an individually reverse-transcribed RNA molecule without detectable amplification bias.

Example 2: TdT Blocks Circularization

Figure 1:
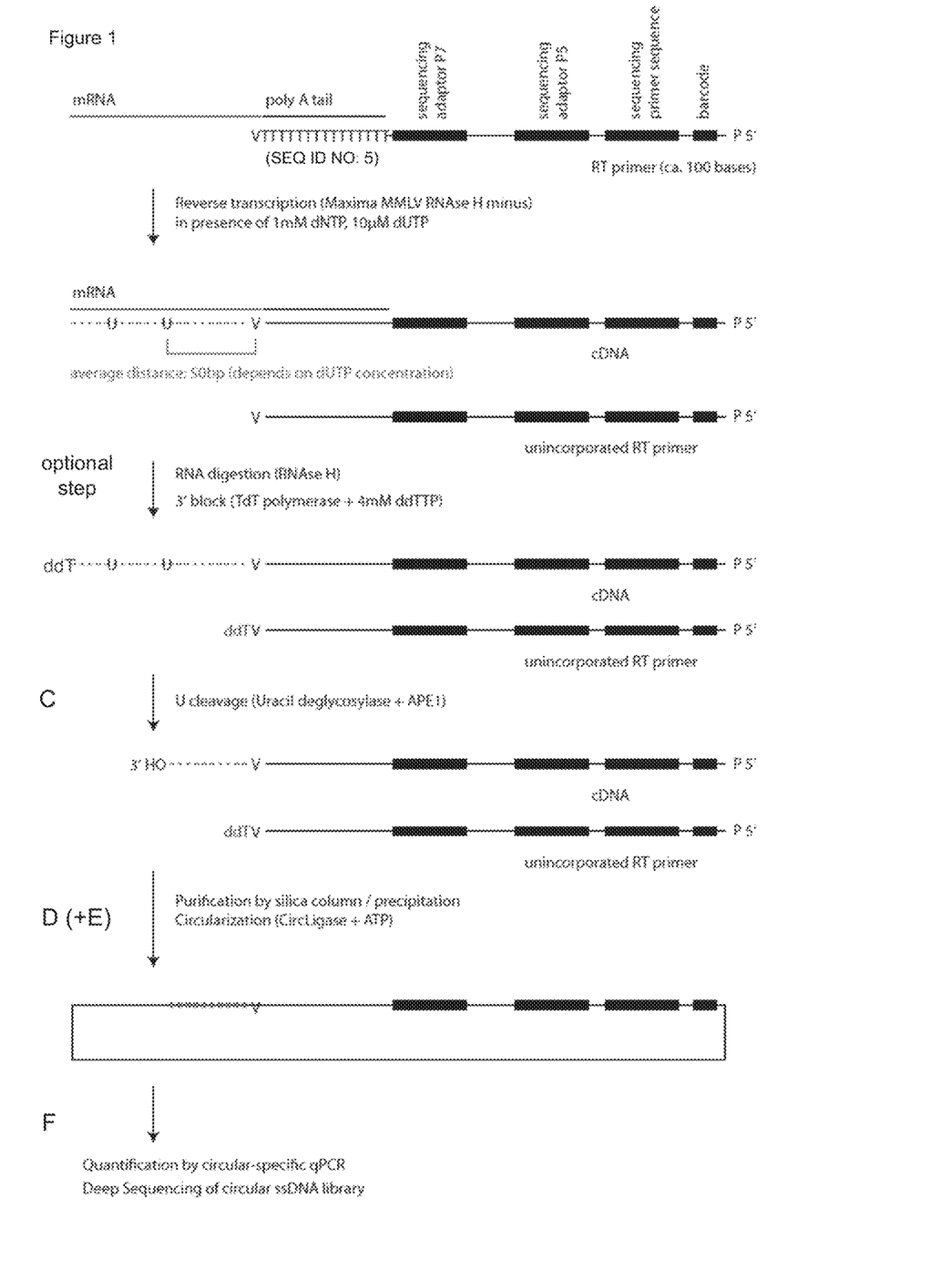
Figure 2:
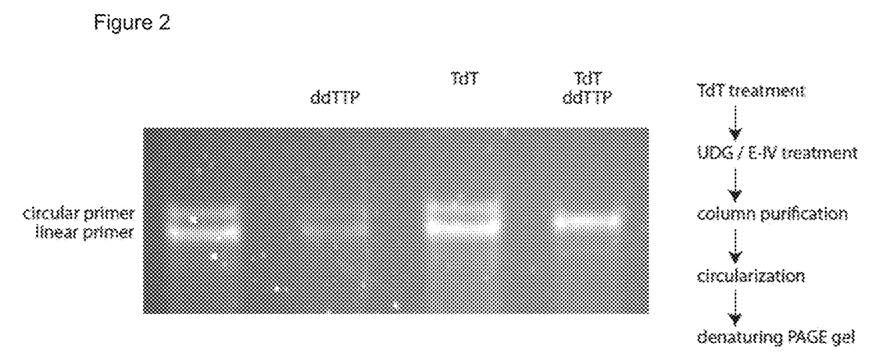
FIG. 2 shows a PAGE gel of circular and/or linear primer molecules (lane 1) in dependence of treatment with ddTTP or TDT alone (lanes 2 and 3) or combined treatment with ddTTP and TDT (lane 4) before CircLigase circularization.

To test the blocking reaction of 3 ends of primers in order to prevent circularization of the molecules, linear primers were incubated with ddTTPs or TdT separately or with ddTTPs and TdT (protocol 1.4. without RNA input) before they were purified on a column (protocol 1.7.) and then treated with CircLigase (protocol 1.8.) to induce circularization of the molecules. The products are then separated on a PAGE gel and stained by SYBR gold (Life technologies). The results as shown in FIG. 2 indicate that ddTTPs and TdT alone do not impair subsequent primer circularization, while ddTTP and TdT together efficiently block primers for later circularization.

Figure 3:
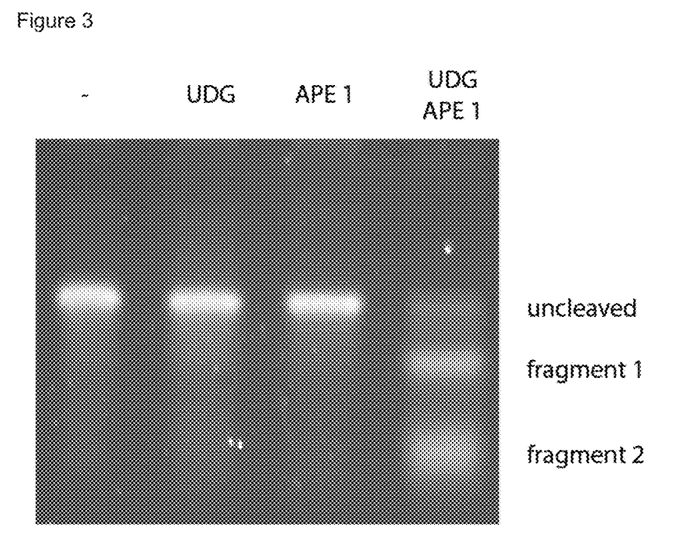
FIG. 3 shows that the combination of the enzymes UDG and APE1 can efficiently cleave dU-modified ssDNA molecules (lane 4 of the agarose gel picture) while each of the enzymes alone fails to cleave the ssDNA (lanes 2 and 3).

Example 3: Uracil Deglycosylase and APE1 in Concert Efficiently Cleave ssDNA at dU Residues in Presence of Reverse Transcription Buffer 10 pmoles of a single stranded 60-mer ssDNA oligonucleotide containing a single dU residue were incubated for 1 hour at 37° C. in 1× reverse transcription buffer with either 0.5 µl UDG, 1 µl APE1, or both. Fragmentation was monitored on a 6% denaturing PAGE gel stained with SYBR gold. FIG. 3 shows that the combination of UDG and APE1 efficiently cleave the oligonucleotide whereas each of the enzymes alone failed to do so.

The invention claimed is:

1. A method for gene analysis comprising:
   a) providing nucleic acid;
   b) transcribing the nucleic acid to form single-stranded DNA by contacting the nucleic acid with a DNA polymerase, a primer and a mixture of dNTPs under conditions that allow the generation of the DNA, wherein the primer comprises a target-complementary region and wherein the dNTP mixture comprises dATP, dGTP, dCTP, dTTP and dUTP, wherein the molar concentration of dUTP is about 0.01 to 20% of the molar concentration of dTTP, and wherein the amounts of dATP, dGTP, dCTP and (dTTP+dUTP) are essentially equimolar;
   c) cleaving the DNA 5' to dU sites by (i) contacting the DNA with an Uracil Deglycosylase to generate abasic sites at positions of dUTP incorporation in the DNA; and (ii) contacting the DNA with an apurinic/apyrimidinic (AP) endonuclease;
   d) optionally purifying the DNA comprising at its 5'-end the nucleotide sequence of the primer;
   e) contacting the DNA comprising at its 5'-end the nucleotide sequence of the primer with a ssDNA ligase to circularize the DNA comprising at its 5'-end the nucleotide sequence of the primer; and
   f) sequencing the circularized DNA.

2. The method of claim 1, wherein the nucleic acid of process a) is provided in form of a sample and is selected from genomic DNA and or cellular RNA.

3. The method of claim 2, wherein the cellular mRNA is mRNA.

4. The method of claim 3, wherein the mRNA is eukaryotic mRNA comprising a plurality of different mRNAs.

5. The method of claim 3, wherein transcribing the nucleic acid to form single-stranded DNA comprises
   (i) reverse-transcribing the mRNA to form single-stranded cDNA by contacting the mRNA with a RNA-dependent DNA polymerase and a universal RT primer under conditions that allow the generation of the cDNA, wherein the universal RT primer comprises at its 3'-end a target-complementary region comprising or consisting of a poly(dT)-dV-3'OH or poly(dT)-dV-dN-3'OH sequence to facilitate hybridization to the polyadenylation sequence of the mRNA, wherein the poly (dT) sequence is 5 to 50 nucleotides in length and V is A, C or G and N is A, C, G or T; and
   (ii) digesting the mRNA by contacting it with an RNAse at any time after step (a) and prior to step e).

6. The method of claim 1, wherein the primer comprises a 3' target-complementary region and at its 5'-end any one or more target non-complementary regions selected from the group consisting of: a unique identifier (barcode) sequence, a sequencing primer binding site and optionally one or more sequencing adapter sites, a 5' mono-phosphorylation or 5'-adenylation, a detectable label, and a non-base spacer.

7. The method of claim 1, wherein the primer is an universal RT primer and comprises in 3' to 5' orientation either (a) a target-complementary region, a sequencing adapter, optionally a blocking spacer, optionally a detectable label, optionally a second sequencing adapter, a sequencing primer binding-site, and an identifier barcode sequence or (b) a target-complementary region, an identifier barcode sequence, a sequencing primer binding-site, a sequencing adapter, optionally a blocking spacer, optionally a detectable label, and optionally a second sequencing adapter.

8. The method of claim 1, wherein the method further comprises the process of blocking the 3' ends of non-extended primer molecules and the generated DNA molecules by use of a terminal deoxynucleotide (TdT) in the presence of at least one dideoxynucleotide triphosphate (ddNTP), wherein said process is performed after process b) and prior to process c).

9. The method of claim 1, wherein the method further comprises the process of quantifying the circularized DNA prior to the sequencing process f).

10. The method of claim 1, wherein the method further comprises degrading the DNA by contacting the DNA with an exonuclease prior to the sequencing process.

11. The method of claim 1, wherein processes a) and b) are performed for a plurality of different nucleic acid or mRNA populations, wherein for each population a universal (RT) primer with a different unique identifier sequence is used, wherein the thus generated plurality of DNA molecules is then combined for all subsequent method processes.

12. The method of claim 1, wherein process d) comprises precipitation, chromatography, column purification, and/or gel electrophoresis.

13. The method of claim 1, wherein process a) comprises isolating the nucleic acid from a sample.

* * * * *